US00PP15574P3

(12) United States Plant Patent
Lim et al.

(10) Patent No.: US PP15,574 P3
(45) Date of Patent: Feb. 22, 2005

(54) SHRUB ROSE PLANT NAMED 'BAICREAM'

(50) Latin Name: *Rosa hybrida*
Varietal Denomination: BAIcream

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 159 days.

(21) Appl. No.: 10/385,499

(22) Filed: Mar. 12, 2003

(65) Prior Publication Data

US 2004/0181837 P1 Sep. 16, 2004

(51) Int. Cl.[7] ..... A01H 5/00
(52) U.S. Cl. ..... Plt./104

(58) Field of Search ..... Plt./102, 104, 103, Plt./141, 144, 145, 130, 133, 134

*Primary Examiner*—Howard J. Locker
(74) *Attorney, Agent, or Firm*—Burns, Doane, Swecker & Mathis, L.L.P.

(57) ABSTRACT

A new and distinct variety of Landscape Shrub rose plant is provided which abundantly forms on a recurrent basis creamy white double blossoms with a hint of pink that commonly have a diameter of approximately 10 cm. The buds are slender in configuration and lemon yellow in coloration. The plant exhibits a vigorous, upright and bushy growth habit, and forms attractive foliage that commonly possesses a tint of red-purple when young and assumes a semi-glossy medium green coloration when mature. Very good resistance to Blackspot and Powdery Mildew is displayed. The foliage coloration contrasts nicely with the creamy white blossom coloration. The new variety is particularly well suited for growing as attractive ornamentation in parks and gardens.

2 Drawing Sheets

Botanical/commercial classification: *Rosa hybrida*/Landscape Shrub Rose Plant.
Varietal denomination: cv. 'BAIcream'.

SUMMARY OF THE INVENTION

The new variety of *Rosa hybrida* Landscape Shrub rose plant was created at Yamhill, Oreg., U.S.A., during 1992 by artificial pollination wherein two parents were crossed which previously had been studied in the hope that they would contribute the desired characteristics. The female parent (i.e., the seed parent) was the 'AUSmas' variety (non-patented in the United States). The 'AUSmas' variety is marketed under the Graham Thomas trademark. The male parent (i.e., the pollen parent) was the 'BUCbi' variety (U.S. Plant Pat. No. 4,225). The 'BUCbi' variety is marketed under the Carefree Beauty trademark. The parentage of the new variety can be summarized as follows:

'AUSmas'×'BUCbi'.

The seeds resulting from the above pollination were sown and plants were obtained which were physically and biologically different from each other. Selective study resulted in the identification of a single plant of the new variety having the distinctive ornamental characteristics hereafter described.

It was found that the new variety of the present invention:

(a) exhibits a vigorous, upright and bushy growth habit, (b) forms slender lemon yellow buds, (c) abundantly forms on a recurrent basis attractive creamy white double blossoms with a hint of pink commonly having a diameter of approximately 10 cm, (c) forms attractive foliage that commonly possesses a tint of red-purple when young and assumes a semi-glossy medium green coloration when mature, (d) displays very good resistance to Blackspot and Powdery Mildew, and (e) is particularly well suited for growing as attractive ornamentation in parks and gardens.

Strong canes are formed by the new variety.

The new variety of the present invention can be readily distinguished from its parental varieties. More specifically, the 'AUSmas' variety forms rich deep yellow blossoms having approximately 35 petals, and the 'BUCbi' variety forms light rose blossoms having approximately 15 to 20 petals.

The new variety well meets the needs of the horticultural industry and can be grown to advantage in the landscape where attractive ornamentation is desired. The plant can be grown as a specimen or as a mass planting.

The new variety has been found to undergo asexual propagation by budding on an understock and by the rooting of cuttings. Asexual propagation by budding onto 'Dr. Huey' rootstock (non-patented in the United States) first conducted during April 1993 at Yamhill, Oreg., U.S.A., and subsequently by the rooting of cuttings at Phoenix, Ariz., U.S.A., and elsewhere, has shown that the characteristics of the new variety are stable and are strictly transmissible by such asexual propagation from one generation to another.

Initially the new plant was designated 99R508. The new variety subsequently has been named the 'BAIcream' variety, and is being marketed while using the Macy's Pride trademark.

BRIEF DESCRIPTION OF THE PHOTOGRAPHS

The accompanying photographs show as nearly true as it is reasonably possible to make the same in a color illustrations of this character, typical specimens of the new variety. The rose plants of the new variety had been propagated by the rooting of cuttings, were approximately two years of age, and were being grown outdoors during the seasons of 1999 and 2000 at St. Paul, Minn., U.S.A.

DETAILED DESCRIPTION

Figure 1:
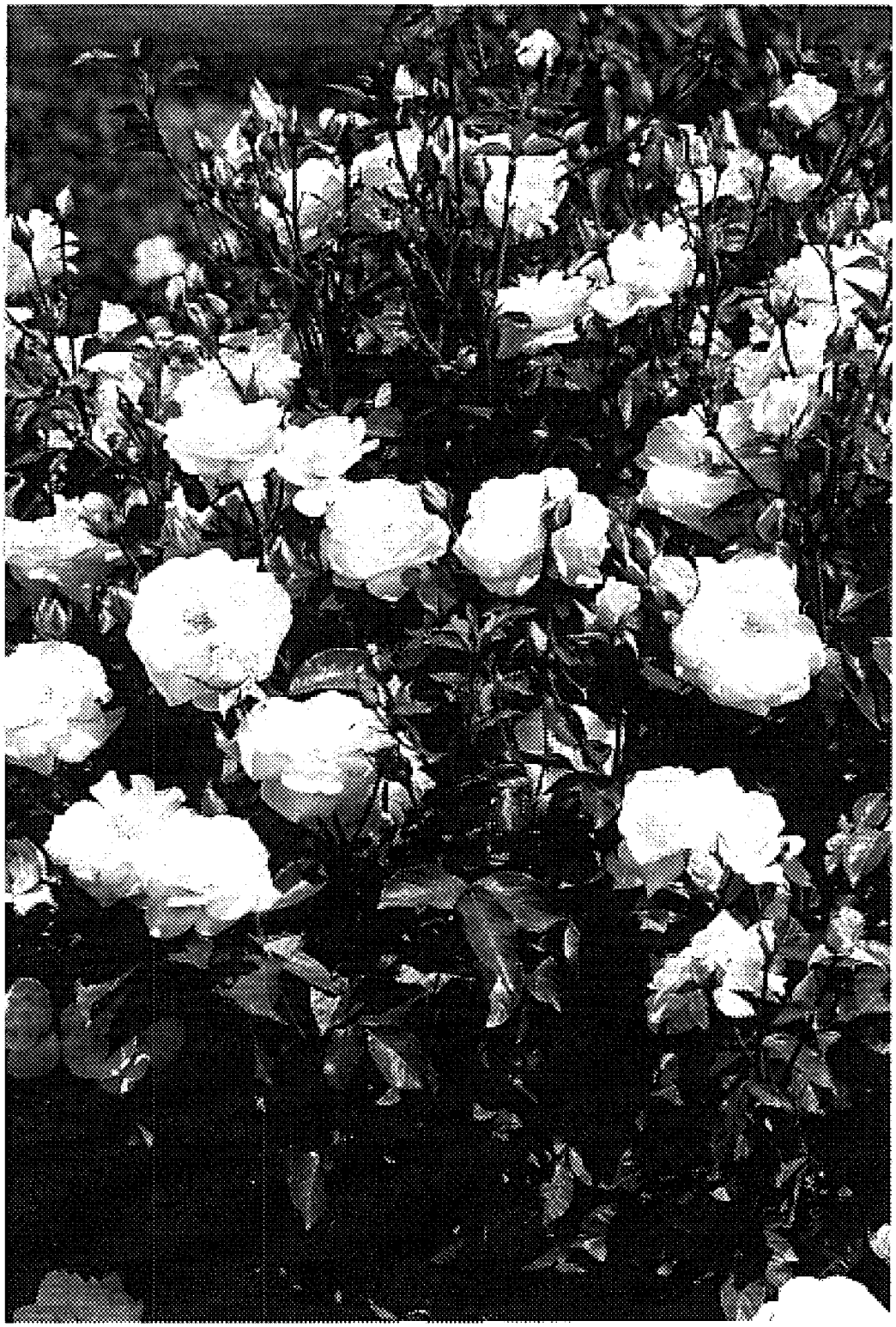
FIG. 1 illustrates typical buds, creamy white blossoms and foliage of the new variety during the summer. The attractive dense semi-glossy medium green foliage is shown.
Figure 2:
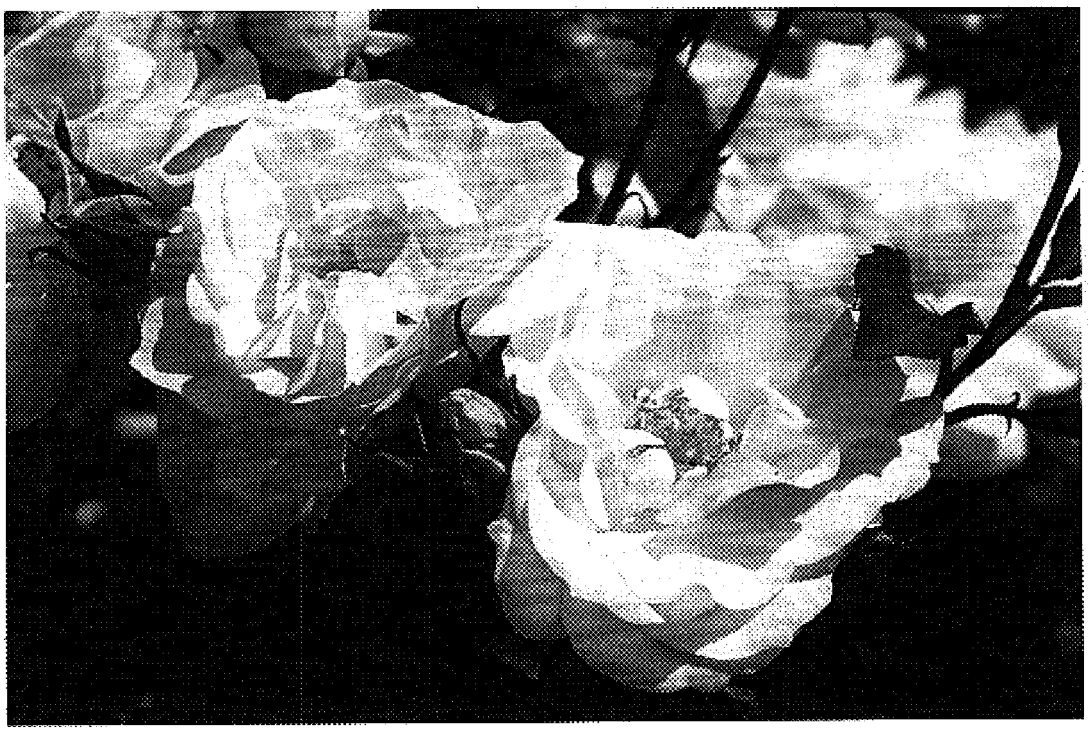
FIG. 2 illustrates a closer view of creamy white blossoms when fully open and buds of the new variety.

The chart used in the identification of the colors is that of The Royal Horticultural Society (R.H.S. Colour Chart). Common color terms are to be accorded their ordinary dictionary significance. The description is based on the observation of two and three year-old plants while growing on their own roots outdoors during June and July 2001 at St. Paul, Minn., U.S.A., and one year-old plants growing outdoors on their own roots during October 2001 at Phoenix, Ariz., U.S.A.

Botanical classification: *Rosa hybrida,* var. 'BAIcream'.
Class: Landscape Shrub Rose.
Plant:
- *Height.*—Approximately 1.5 m on average at the end of the growing season.
- *Width.*—Approximately 1.5 m on average at the end of the growing season.
- *Habit.*—Upright and bushy.

Branches:
- *Color.*—Young stems: new Yellow-Green Group 144B with some highlights of Red Group 53B. Adult wood: Yellow-Green Group 144A.
- *Thorns.*—Size: Commonly approximately 0.5 to 0.75 cm in length on average. Color: commonly between Greyed-Purple Group 184B.

Leaves:
- *Stipules.*—Generally parallel with the auricle facing outward.
- *Petioles.*—Upper surface: Yellow-Green Group 146A. Under surface: Yellow-Green Group 146C.
- *Leaflets.*—Number: 3, 5, and 7 (most often) on mature branches. Shape: ovate with a rounded base and an acuminate tip. Serration: finely serrate. Texture: leathery. General appearance: dense, semi-glossy aspect, and medium green in coloration. Color (young foliage): Upper surface: Yellow-Green Group 146B with highlights of Red-Purple Group 59B. Under surface: Yellow-Green Group 147A with highlights of Red-Purple Group 59A Color (Adult foliage): Upper surface: commonly between Green Group 137A and Yellow-Green Group 147B. Under surface: Green Group 138B with some presence of Green Group 139C.

Inflorescence:
- *Number of flowers.*—Commonly in clusters of three per stem.
- *Peduncle.*—With some prickles, medium green, commonly Green Group 143C in coloration, and the length is approximately 6 cm on average.
- *Sepals.*—Upper surface: between Green Group 143A and 143B in coloration. Under surface: Green Group 143D with areas of White Group 155D, and some pubescence. Size: approximately 3 cm in length with some extensions.
- *Buds.*—Shape: Slender. Size: medium. Length: approximately 3.5 cm on average. Diameter: approximately 1.75 cm on average. Color: Upper surface: commonly between Yellow-Green Group 150D and Yellow-Green Group 154D with highlights of Red-Purple Group 58B. Under surface: commonly between Green-Yellow Group 1C and Yellow-Green Group 154C.
- *Flower.*—Shape: double. Diameter: approximately 10 cm on average. Color (when opening begins): Upper surface: Yellow-Green Group 154C and 154D. Under surface: Green-Yellow Group 1D with highlights of Green-Yellow Group 1B. Color (when blooming): Upper surface: between Yellow Group 2D and Yellow Group 4D with highlights of Red-Purple Group 62C. Under surface: Green-Yellow Group 1D with highlights of Yellow Group 4C and Red-Purple Group 63D. Color (end of blooming): Upper surface: White Group 155B with highlights of Yellow Group 4D. Under surface: White Group 155A with highlights of Yellow Group 2D. Basal petal spot: White Group 155D. Fragrance: slight musk. Lasting quality: the blossoms commonly last approximately 3 to 5 days from bud on the plant on average depending upon the temperature, and the level of sunlight. Petal number: approximately 22 on average under normal growing conditions. Petal shape: wedge-shaped commonly with a curled apex when fully open. Petal drop: the petals drop easily. Stamen number: approximately 75 on average. Anthers: Greyed-Orange Group 163B in coloration. Filaments: Yellow Group 6A in coloration. Pistils: approximately 26 on average. Stigmas: Yellow Group 13B in coloration. Styles: Yellow-Green Group 154A in coloration. Receptacle: separate and free. Hips: ovoid in configuration. Seeds: Greyed-Orange Group 164B with highlights of Greyed-Orange Group 166C in coloration, rugose at the apex with villose hairs, and oval to round in shape.

Development:
- *Vegetation.*—Vigorous.
- *Blooming.*—Abundant at first bloom and then recurrent throughout the growing season.
- *Resistance to diseases.*—Very good resistance to Blackspot, and Powdery Mildew.
- *Aptitude to bear fruit.*—Good.
- *Hardiness zone.*—Zone Nos. 4 to 7.

We claim:

1. A new and distinct variety of Landscape Shrub rose plant characterized by the following combination of characteristics:

(a) exhibits a vigorous, upright and bushy growth habit, (b) abundantly forms on a recurrent basis attractive creamy-white double blossoms with a hint of pink commonly having a diameter of approximately 10 cm, (c) forms attractive foliage that commonly possesses a tint of red-purple when young and assumes a semi-glossy medium green coloration when mature, (d) displays very good resistance to Blackspot and Powdery Mildew, and (e) is particularly well suited for growing as attractive ornamentation in parks and gardens;

substantially as herein shown and described.

* * * * *